(12) United States Patent
Shulman

(10) Patent No.: US 10,000,777 B2
(45) Date of Patent: *Jun. 19, 2018

(54) METHOD FOR EMPLOYING CORN PLANT MATERIAL COMPRISING COBS IN THE MANUFACTURE OF ETHANOL

(71) Applicant: Alvin D. Shulman, Highland Park, IL (US)

(72) Inventor: Alvin D. Shulman, Highland Park, IL (US)

(*) Notice: Subject to any disclaimer, the term of this patent is extended or adjusted under 35 U.S.C. 154(b) by 0 days. days.

This patent is subject to a terminal disclaimer.

(21) Appl. No.: 14/710,293

(22) Filed: May 12, 2015

(65) Prior Publication Data

US 2015/0247166 A1 Sep. 3, 2015

Related U.S. Application Data

(63) Continuation of application No. 13/571,581, filed on Aug. 10, 2012, now Pat. No. 9,062,327, which is a continuation of application No. 12/723,149, filed on Mar. 12, 2010, now Pat. No. 8,247,202, which is a continuation of application No. 11/623,146, filed on Jan. 15, 2007, now Pat. No. 7,682,810.

(51) Int. Cl.
*C12P 7/06* (2006.01)

(52) U.S. Cl.
CPC .............. *C12P 7/06* (2013.01); *Y02E 50/17* (2013.01)

(58) Field of Classification Search
CPC .................................. C12P 7/06; Y02E 50/17
See application file for complete search history.

(56) References Cited

U.S. PATENT DOCUMENTS

| | | | |
|---|---|---|---|
| 4,139,952 A | 2/1979 | Stanfield | |
| 4,245,948 A | 1/1981 | Kersten | |
| 4,509,273 A | 4/1985 | Roisen | |
| 5,941,768 A | 8/1999 | Flamme | |
| 6,358,141 B1 | 3/2002 | Stukenholtz et al. | |
| 8,247,202 B2 * | 8/2012 | Shulman | C12P 7/06 435/161 |
| 9,062,327 B2 * | 6/2015 | Shulman | C12P 7/06 |
| 2004/0045215 A1 | 3/2004 | Guilfoyle | |
| 2004/0091983 A1 | 5/2004 | Veit et al. | |
| 2008/0006536 A1 | 1/2008 | Cuomo et al. | |

OTHER PUBLICATIONS

Oxbo International Corporation, Products 8420 XP Power Unit (2 pg. web brochure), http://www.oxbocorp.com/prod8420.html, Copyright 2005 by OXBO International Corporation & Web Centers of America, Inc.
Oxbo International Corporation, Products 9400 Power Unit (2 pg web brochure), http://www.oxbocorp.com/prod9400.html, Copyright 2005 by OXBO International Corporation & Web Centers of America, Inc.
Oxbo International Corporation, Products 9620 Power Unit (1 pg web brochure), http://www.oxbocorp.com/prod9620.html, Copyright 2005 by OXBO International Corporation & Web Centers of America, Inc.
Oxbo International Corporation, Products Big Jack™ Harvester (3 pg web brochure), http://www.oxbocorp.com/prod_bigjack.html, Copyright 2005 by OXBO International Corporation & Web Centers of America, Inc.
Oxbo International Corporation, Products Super™ Jack Harvester (2 pg web brochure), http://www.oxbocorp.com/prod_superjack.html, Copyright 2005 by OXBO International Corporation & Web Centers of America, Inc.
Oxbo International Corporation, Products EL 30 Harvester (2 pg web brochure), http://www.oxbocorp.com/prod_el30.html, Copyright 2005 by OXBO International Corporation & Web Centers of America, Inc.
Oxbo International Corporation, Products 2480 Multi-Crop Harvester (2 pg web brochure), http://www.oxbocorp.com/prod_leg2480.html, Copyright 2005 by OXBO International Corporation & Web Centers of America, Inc.
Oxbo International Corporation, Products 3000 Series Corn Head (2 pg web brochure), http://www.oxbocorp.com/prod_3000.html, Copyright 2005 by OXBO International Corporation & Web Centers of America, Inc.
Oxbo International Corporation, Products 3000 Series Folding Corn Head (2 pg web brochure), http://www.oxbocorp.com/prod_foldingcornhead.html, Copyright 2005 by OXBO International Corporation & Web Centers of America, Inc.
Broeren, Margaret, Putting Less Energy Into Bioenergy Crops, CALS News, pp. 1 3, College of Agricultural &Life Sciences, University of Wisconsin-Madison, http://news.cals.wisc.edu/newsDisplay.asp?id=1547, Sep. 25, 2006 (e pages).
Atchison, J.E., et al., Innovative Methods for Corn Stover Collecting, Handling, Storing and Transporting, Mar. 2003, pp. i-ix, I-16, 24-25 and 37-45, National Renewable Energy Laboratory, Golden, Co.
Krapfl, Mike, Iowa State Researchers Developing Machinery to Harvest Corn Stalks and Leaves. PMN, Crop Management, pp. 1 2, Dec. 19, 2006 Iowa State University, Ames, IA. http://www.plantmanagementnetworks.org/pub/cm/news/2006/Machinery/.
U.S. Department of Energy, Biomass Program Integrated Corn Based Bio Refinery, Apr. 2006, U.S. Department of Energy, Office of Energy Efficiency and Renewable Energy, Washington, D.C. http://www1.eere.energy.gov/biomass/pdfs/corn-based_biorefinery.pdf.

(Continued)

*Primary Examiner* — Renee Claytor
*Assistant Examiner* — Susan E. Fernandez
(74) *Attorney, Agent, or Firm* — Marshall, Gerstein & Borun LLP

(57) ABSTRACT

Ear corn is picked from corn fields by ear corn harvesters and transported to a central shelling station associated with an ethanol manufacturing facility. Shelled corn from the central shelling station is processed into ethanol at the ethanol manufacturing facility, and corn cobs from the central shelling station are burned to provide process heat for the ethanol manufacturing process. Energy is conserved and costs are reduced during the picking and shelling of the ear corn and by the burning of cobs for process heat.

45 Claims, 1 Drawing Sheet

(56) References Cited

OTHER PUBLICATIONS

Keener, "Shelled Corn as an Agri-Fuel: Direct Combustion vs. Ethanol" OCAMM (Ohio Composting and Manure Management) program Jan. 2009 <http://www.oardcl.ohio-state-edu/ocamm/keener3.htm>.

Butler, "Nebraska Corn Stover Removal Analysis" [<http://www.neo.ne.gov/publications/Feasibility_Corn_Residue_Collection_Kearney-1993.pdf>]Apr. 1993 Appendix I, pp. 29-48.

Vagts, "Reducing Harvest Losses in Lodged Corn Fields" [www.etension.iastate.edu/nwcrops/reducing-harvest-losses.htm] Jun. 7, 2005.

Van Dyke, "Innovative Solution to High Energy Costs," Feed & Grain, Apr./May 2006, pp. 31-32, vol. 45, No. 3; www.feedandgrain.com.

Claar, Paul W. II, et al., "Economic and Energy Analysis of Potential Corn-Residue Harvesting Systems," Agricultural Energy, vol. 2, Biomass Energy Crop Production, 1981, pp. 273-279, American Society of Agricultural Engineers, St. Joseph, Michigan.

Quick, Graeme, et al., "Single-Pass Corn and Stover Harvesting Developments," 2002, Iowa State University, Ames, Iowa.

Liljedahl, J.B., et al., "Cob Harvesting and Biomass Storage Systems," 1983, pp. 225-228, 3rd Annual Solar and Biomass Workshop, Southern Agricultural Energy Center, Atlanta, Georgia.

Smith, R.D., et al., "Corncob Collection During Grain Harvest," 1984, pp. 76-79, 4th Annual Solar and Biomass Energy Workshop, Southern Agricultural Energy Center, Atlanta, Georgia.

Gustafson, Cole, et al., "Harvesting Both Corn Grain and Stover in Adverse Weather," Ethanol Producer Magazine, Sep. 2011, pp. 66-69.

Erickson, Matthew J., et al., "The Economics of Harvesting Corn Cobs for Energy,".

BioEnergy, 2010, Purdue University, West Lafayette, Indiana, http://mdc.itap.purdue.edu/item.asp?itemID=19701.

"Vermeer CCX770 Cob Harvester," copyright Nov. 2010, Vermeer Corporation, Pella, Iowa, http://www2.vermeercom/vermeer/NA/en/N/equipment/cob_harvester/ccx770.

Schechinger, Tom M., et al., "Corn Stover Harvest," Grower, Custom Operator, and Processor, Issues and Answers, 1999, pp. 1-4, 10-16, 39-40, 53-54, B-2-B6, Oak Ridge National Laboratory, Oak Ridge, Tennessee.

\* cited by examiner

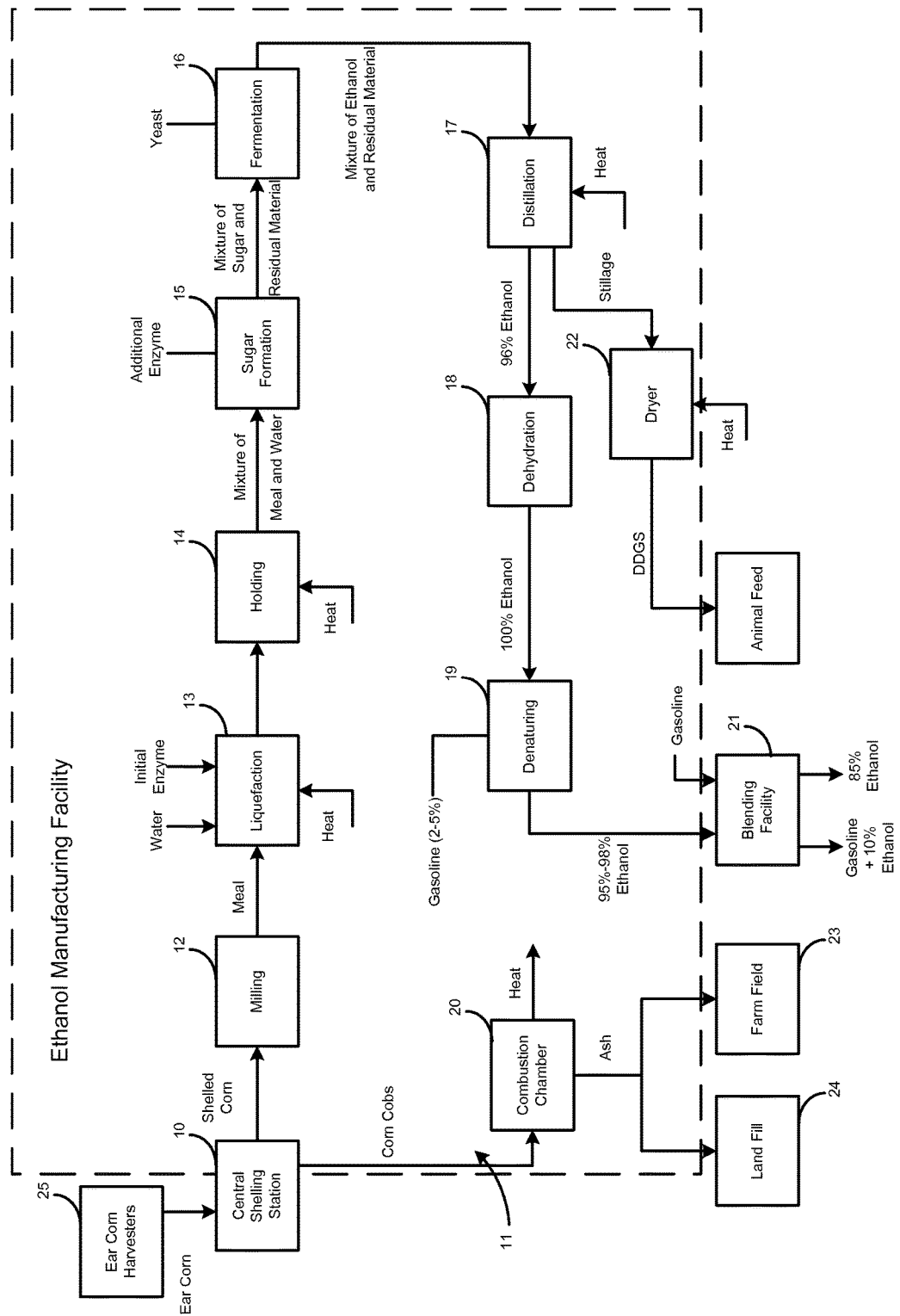

METHOD FOR EMPLOYING CORN PLANT MATERIAL COMPRISING COBS IN THE MANUFACTURE OF ETHANOL

RELATED APPLICATION

This is a continuation of application Ser. No. 13/571,581, filed Aug. 10, 2012, now U.S. Pat. No. 9,062,327 issued Jun. 23, 2015, in turn a continuation of application Ser. No. 12/723,149, filed Mar. 12, 2010, now U.S. Pat. No. 8,247,202, dated of Aug. 21, 2012, in turn a continuation of application Ser. No. 11/623,146, filed Jan. 15, 2007, now U.S. Pat. No. 7,682,810, dated Mar. 23, 2010, the contents of which are hereby incorporated herein by reference.

FIELD OF THE INVENTION

The present invention relates generally to the manufacture of ethanol from corn and more particularly to the conservation of fuel and reduction of costs during the ethanol manufacturing process and during the harvesting and shelling of the corn.

BACKGROUND OF THE INVENTION

Ethanol is blended with gasoline for use as a fuel in vehicles with internal combustion engines. A blend containing 10% ethanol as an additive produces a cleaner burning gasoline. A blend containing 85% ethanol is used as a substitute for gasoline.

Ethanol can be manufactured from a number of domestically grown vegetative materials including corn, sugar cane and sugar beets. The manufacture of ethanol from domestically grown crops reduces the reliance on imported petroleum as a source for fuel for internal combustion engines. Corn is the largest domestically grown crop from which ethanol is manufactured.

Corn in a farm field is conventionally harvested by a combine, a self-propelled piece of equipment which picks the ears of corn from the corn stalks, separates the corn kernels from the corn cobs (shelling) and from the husks on the ears of corn, and returns the cobs and husks to the farm field. The shelled corn is temporarily stored in the combine and then transferred to a vehicle that transports the shelled corn to a storage facility. The cobs and husks that have been returned to the farm field, together with the stalks and leaves left on the field, are collectively known as stover, a material which beneficially helps to build soil and prevent erosion when left in the field.

Combines came into widespread use for harvesting corn in the latter half of the twentieth century. Prior to that, corn was hand picked, or it was picked by a mechanical corn picker that was mounted on or towed by a tractor and that was capable of picking, e.g., one to two rows in a single pass. After the ear corn was picked, it typically was stored on the farm and then shelled by shelling equipment typically mounted on a truck which traveled to the farm and shelled the ear corn on site. The combine replaced both the mechanical picker and the traveling sheller.

Ethanol is made from shelled corn. A multi-stage process is employed to produce ethanol from shelled corn, and some of these stages require heat supplied by the combustion of fuel, typically natural gas. Natural gas is also consumed (a) during the production of nitrogen fertilizer applied to the farm field where the corn is grown and (b) to a lesser extent, during the production of pesticides used on the corn.

Petroleum-based fuels power the vehicles used in the growing and harvesting of corn and in the transporting of corn between the farm fields and the ethanol manufacturing facility.

A drawback to conventional processes for producing ethanol from corn resides in the consumption of large quantities of energy during the ethanol manufacturing process and during the growing, harvesting and transporting of the corn. As noted above, this energy is consumed in large part by the combustion of natural gas and of petroleum-based vehicle fuel. When ethanol from corn is produced at a processing plant dedicated exclusively to the production of ethanol, the ratio of (a) the energy available from the ethanol to (b) the energy equivalent of the total fossil fuel input is 1.77. (Total fossil fuel input comprises both natural gas and petroleum-based vehicle fuel.)

The amount of energy consumed during (i) the conversion of corn to ethanol, at the ethanol manufacturing facility, is about twice the energy consumed in (ii) corn production, which includes the manufacture of fertilizer and pesticides with natural gas, as well as the operation of the farming equipment with petroleum-based fuel. Items (i) and (ii) above together constitute at least 90% of the total energy consumed. The remainder (less than 10%) is consumed in transporting the shelled corn to the ethanol manufacturing facility and in the post-production distribution of the ethanol by truck, rail and the like.

Attempts have been made to conserve the natural gas consumed during the ethanol manufacturing process by replacing the natural gas with a renewable fuel. In one such instance, the fuel was cattle manure from a massive cattle feeding lot next to which the ethanol manufacturing facility was located to eliminate the cost of transporting the manure which could otherwise be a prohibitive expense. There are, however, only a limited number of locations where this type of operation can be employed.

A residual product of the ethanol manufacturing process is a mash known as "stillage" which is dried and sold as animal feed. The dried stillage is also called "dried distiller's grain and solubles" or DDGS.

There have been proposals to use DDGS, or stover, or a combination of the two, as fuel to produce process heat for the ethanol manufacturing process. In some proposals, the material is used to fuel a cogeneration plant that produces (a) electricity to power equipment employed at the ethanol manufacturing facility and (b) steam for use as the heating medium in stages of the ethanol manufacturing process that require heat. A cogeneration plant is a substantial capital expense.

With respect to the use of stover as a fuel, there are some drawbacks. The stover has to be gathered from the field and baled for more efficient handling and transportation and then transported to the ethanol manufacturing facility, all of which entails expense and consumes fuel. Moreover, when stover is removed from the field, this deprives the field of the benefits arising when stover is left in the field (soil building and erosion prevention).

As noted above, corn intended for subsequent processing into ethanol is conventionally harvested with a combine that both picks and shells the corn. Seed corn and sweet corn are harvested by another type of self-propelled equipment known as an ear corn harvester which picks the corn but does not shell it. In the case of seed corn, the ear corn, after harvesting, is stored and dried and then shelled by a piece of equipment separate and discrete from the earn corn harvester. This protects the corn kernels that are to be used as seed, from damage that can occur when shelling is performed by a combine. Damaged corn kernels are unsuitable for use as seed.

In rural corn-growing areas, during the first half of the twentieth century and earlier, corn cobs were used as kindling for coal-burning, home heating furnaces and hot water heaters. In some rural areas, during the depression in the 1930's and during the war years in the 1940's, ear corn was used as a substitute for coal in home heating furnaces.

Stanfield U.S. Pat. No. 4,139,952 discloses a procedure in which ears of seed corn are dried by heat generated at an incinerator and then shelled to produce (a) kernels of seed corn and (b) corn cobs that are employed as fuel for the incinerator.

It is possible to produce ethanol from cellulose contained in stover. However, it is currently much more difficult to produce ethanol from stover than from shelled corn, and substantially more expensive. At the present time production of ethanol from stover is not economically attractive.

SUMMARY OF THE INVENTION

In the present invention, corn cobs are used as fuel in the ethanol manufacturing process. In the farm field, the combine is replaced by an ear corn harvester. Quantities of ear corn harvested by a plurality of ear corn harvesters are transported to a central shelling station located at or next to, or otherwise associated with, the ethanol manufacturing facility. At the central shelling station, the ear corn is shelled to separate the corn kernels from the corn cobs, the shelled corn is conveyed to the first stage of the ethanol manufacturing process, and the corn cobs are combusted to produce heat for the process Compared to conventional practice, energy is conserved in the harvesting of the corn, in the shelling of the corn and in the combustion of fuel to provide heat for the ethanol manufacturing process. Operating costs are reduced at the farm, at the central shelling station and at the ethanol manufacturing facility.

Other features and advantages are inherent in the invention claimed and disclosed or will become apparent to those skilled in the art from the following detailed description, much of which is a projection, in conjunction with the accompanying flow diagram.

BRIEF DESCRIPTION OF THE DRAWING

FIG. 1 is a flow diagram illustrating an embodiment of a method in accordance with the present invention.

DETAILED DESCRIPTION OF THE PREFERRED EMBODIMENTS

Referring to the flow diagram of FIG. 1, indicated generally at 11 (and contained within dashed lines in FIG. 1) is an ethanol manufacturing facility which performs a multi-stage process for converting shelled corn into ethanol. Some of the processing stages require heat which is provided by combusting fuel at a combustion chamber 20 located within facility 11.

A central shelling station 10 is located at or next to (i.e., physically associated with) ethanol manufacturing facility 11, or is otherwise associated with facility 11. Ear corn harvested from a number of farm fields by a plurality of ear corn harvesters 25 is transported to central shelling station 10 where the ear corn is shelled to separate the corn kernels from the corn cobs. As used herein, the term "central shelling station" refers to a stationary piece of shelling equipment that shells ear corn harvested by a plurality of ear corn harvesters.

The shelled corn from central shelling station 10 is conveyed to the first stage 12 of ethanol manufacturing facility 11 where the shelled corn is milled. The shelled corn may be directly conveyed to first stage 12, or it may be temporarily stored in silos or the like for subsequent conveyance to first stage 12.

Corn cobs from shelling station 10 are conveyed to combustion chamber 20 where the cobs are combusted to provide some or all of the heat for those stages of the process that require heat. The cobs from shelling station 10 may be directly conveyed to combustion chamber 20, or they may be held at storage sites adjacent shelling station 10 or adjacent combustion chamber 20 or at other storage sites at facility 11, for subsequent conveyance to and/or introduction into combustion chamber 20.

At first processing stage 12, the shelled corn is ground into a fine powder called meal, and the meal is then conducted to a liquefaction stage 13 where water and an initial enzyme (alpha amylase) are added and mixed with the meal. The resulting mixture is then passed through cookers where heat is applied to liquefy the starch in the meal. The cookers comprise an initial stage at 13, where the mixture is cooked at a relatively high temperature (e.g., 100°-150° C.) to reduce bacteria levels in the mixture, followed by a holding stage 14 where the mixture is maintained at a lower temperature (e.g. 95° C.), with additional heat, if required.

From holding stage 14, the cooked mixture is conducted to a sugar formation stage 15 where additional (secondary) enzyme is added (e.g., glucoamylase), to convert the starch in the mixture to fermentable sugars (e.g., dextrose). The resulting mixture of sugar and residual material is then conducted to a fermentation stage 16 where yeast is added to ferment the sugars into ethanol. During fermentation, large quantities of carbon dioxide gas ($CO_2$) are emitted, and this additional reaction product can be captured, compressed and sold commercially.

Fermentation may be continuous wherein the sugar-containing mixture flows through a series of fermenting sub-stages until the sugars are fully fermented; or fermentation may be conducted as a batch process in which the sugar-containing mixture is held in one fermenting stage for an extended period of time (e.g., 48 hours) until fermentation is complete.

The fermented mixture or mash product at fermentation stage 16 comprises 10% alcohol plus residual, non-fermentable solids from the corn and from the yeast cells. The mash from fermentation stage 16 is then directed to a distillation stage 17 where heat is applied to distill the ethanol from the mash. Typically, the mash is pumped through a continuous flow, multi-stage, distillation system where the ethanol is removed from the solids and separated from the water in the mash to produce 96% strength ethanol which is conducted to a dehydration stage 18 where the remaining water is removed to give 200 proof, anhydrous (no water) ethanol.

The residual mash from distillation stage 17 is called stillage which may be conducted to a dryer 22 where heat is applied to remove water and produce a dried product called distillers dried grain and solubles (DDGS) which has value as an animal feed. Undried stillage may also be employed as an animal feed.

The anhydrous ethanol from dehydration stage 18 is conducted to a denaturing stage 19 where 2-5% gasoline is added to make the ethanol unfit for human consumption. The resulting product is composed of 95-98% ethanol which is then transported to a blending facility 21, typically at a location remote from ethanol manufacturing facility 11. At blending facility 21, the ethanol is mixed with additional gasoline in appropriate proportions that enable the ethanol to be used either as an additive (e.g., a blend with 10% ethanol) or as a fuel (e.g., 85% ethanol).

The heat for liquefaction and holding stages 13, 14, for distillation stage 17 and for dryer 22 is provided by combusting corn cobs from shelling station 10. Combustion typically occurs at combustion chamber 20, but combustion may also be performed at an auxiliary combustion chamber, e.g., a combustion chamber associated with dryer 22. The heating medium for a given heating location may be steam or heated air. The largest part of the total heat requirements for the process is that employed at distillation stage 17. Preferably, combustion chamber 20 is located adjacent distillation stage 17.

The ash produced by the combustion of the corn cobs contains minerals which have some value as fertilizer and can be given away for spreading on a farm field 23 within an economically transportable distance from manufacturing facility 11. Otherwise, the ash is transported to a nearby land fill 24.

Depending upon the quantity of corn cobs produced at the central shelling station, the corn cobs used as fuel replace some or all of the natural gas conventionally used as fuel for the ethanol manufacturing process. Because the corn cobs are a byproduct of the shelling operation conducted at central shelling station 10, they constitute fuel obtained free of charge. In contrast, natural gas is relatively expensive, so that the replacement of natural gas by corn cobs produces substantial cost savings.

Moreover, corn cobs are a renewable fuel source obtained by replanting the corn field from which the cobs were harvested (or an equivalent field); natural gas is not renewable. In addition, the carbon dioxide emitted into the atmosphere by the combustion of corn cobs is offset by the carbon dioxide absorbed from the atmosphere during the growing of the corn; there is no such offset for the carbon dioxide emitted into the atmosphere by the combustion of natural gas.

Central shelling station 10 shells ear corn from a multitude of corn fields where the ear corn was previously conventionally shelled by combines that can be replaced by ear corn harvesters when a central shelling station is employed. The combination of ear corn harvesters and a central shelling station provides several advantages compared to combines.

A typical ear corn harvester can pick six or seven rows of corn in one pass; some models can pick ten rows. (The picking operation is similar to that performed by a combine.) The ears of corn are husked, the husks (and any tramp stover elements) are returned to the field, and the ear corn is conveyed, in one model, to a tiltable dump hopper at the rear of the ear corn harvester. The dump hopper is equipped with a hydraulic lift which is operated to tilt the dump hopper about a high tilt axis to unload the hopper quickly into a truck or semi-trailer having relatively high sides. The quick-unload feature minimizes the time spent by the harvester on activities other than harvesting (i.e., "down time").

In another model, the ear corn is conveyed into a dump cart that runs alongside the ear corn harvester. The dump cart is pulled by a tractor and has the same kind of dump hopper with hydraulic lift described in the preceding paragraph, to facilitate quick unloading.

An ear corn harvester can make a harvesting pass through a corn field at a faster speed than a combine because the speed at which a combine can pick corn is restrained by the rate at which the combine can shell the ear corn the combine has picked. An ear corn harvester has no such restraint and can harvest at cruising speeds, e.g., in the range 18-21 miles per hour. Comparing an ear corn harvester and a combine, each of which can pick the same number of corn rows in a single pass, the ear corn harvester, due to its faster picking speed, will pick a given acreage in a shorter time period than a combine picking the same acreage. Expressed another way, an ear corn harvester can pick a given acreage in the same amount of time as a combine that can pick more rows of corn in a single pass.

The discussion in the following part of this paragraph assumes a situation in which ear corn harvesters and combines each pick the same number of corn rows in a single pass. Given the acreage of corn required to satisfy the annual demand of an ethanol manufacturing facility, that acreage can be harvested during a given harvest season with fewer ear corn harvesters than the number of combines required to harvest the same acreage. As a result, there is less total capital expense when ear corn harvesters are employed, even assuming that an ear corn harvester and a combine cost the same. (Actually, a combine costs more.) There is also less total operational expense, even assuming that the operational expense for a single ear corn harvester is the same as that for a single combine; and there is less total labor expense. Moreover, there is also less total fuel consumed in operating the smaller number of ear corn harvesters, even assuming that a single one of each of the two types of equipment consumes the same amount of fuel during a given period of operation.

In actuality, an ear corn harvester consumes less fuel than a combine harvesting the same number of corn rows in a single pass. This is because, unlike the combine, the ear corn harvester does not consume the fuel required for operating shelling equipment and does not consume the fuel required for transporting the weight of the shelling equipment up and down rows in the corn field. (It is assumed that the weight of the other equipment on the ear corn harvester and combine (e.g. corn picking equipment and corn storage and unloading structure) weigh substantially the same; any substantial difference in the weight of this other equipment could result in a difference in the amount of fuel consumed.) Although the ear corn harvester operates at a faster speed than the combine when picking corn, the combine runs for a longer period of time to pick the same acreage, so that there is probably no substantial difference in the amount of fuel consumed due to picking corn at different speeds. Some of the energy saving attributable to the absence of a shelling function on an ear corn harvester is offset downstream in shelling ear corn at the central shelling station. However, the shelling equipment at the central shelling station is stationary, and unlike a combine, no energy is expended transporting that shelling equipment up and down corn rows.

As noted above, there is a situation where the number of ear corn harvesters employed is the same as the number of combines. In this situation, the combine is large enough to pick more rows in a single pass than the speedier ear corn harvester; but the ear corn harvester still has a cost advantage over the combine. More particularly, each large combine costs more than an ear corn harvester, and the number of pieces of equipment required to harvest the acreage in question is substantial. Accordingly, there will be a substantial saving in total capital expense when employing ear corn harvesters in lieu of large combines; and there should be less operational expense and less fuel consumed when one employs the ear corn harvesters. Labor expense will be the same.

Ear corn harvesters of the types described above are available from the following source: Oxbo International Corporation, 7525 Byron Road, Byron, N.Y., 1422-0100. Brochures describing the ear corn harvesters can be obtained from that company's website: www.oxbocorp.com; and the disclosures therein are incorporated herein by reference.

The use of a single, central shelling station, instead of shelling with a multitude of combines at each of a multitude of individual corn fields, conserves energy in a number of ways. Each of the multitude of combines employed to shell corn in conventional procedures has its own internal combustion engine which runs on a petroleum-based liquid fuel. A central shelling station would employ the efficiencies of scale to shell the same amount of corn with less fuel, assuming the shelling equipment at the central shelling station was powered by an internal combustion engine. However, the central shelling station would most likely be powered by an electric motor driven by electricity from power lines. The electricity obtained from power lines in the corn-growing Midwest is typically generated at a power plant fueled by coal or nuclear fuel. Natural gas or petroleum-based liquid fuels are generally not employed and are thus conserved when a central shelling station is employed.

Moreover, even if the central shelling station were powered by an internal combustion engine, the combination of ear corn harvester and central shelling station would still consume less fuel than the use of a combine to both pick and shell corn. More particularly, and as noted above, when shelling with a combine, fuel is consumed not only to operate the shelling equipment on the combine, but also to move the weight attributable to the shelling equipment up and down the corn rows, and this occurs in each of the multitude of corn fields supplying corn to the ethanol manufacturing plant. In contrast, with a central shelling station, the shelling equipment is stationary, and the fuel consumed in moving the shelling equipment in a combine up and down corn rows is conserved. (This is in addition to the fuel that would be conserved at a central shelling station due to efficiencies of scale).

The capital investment in the shelling equipment at a central shelling station will be substantially less than the cumulative capital investment attributable to the shelling equipment in a multitude of combines shelling the same quantity of corn. This is because the shelling equipment in a combine must be large enough to shell, during the relatively short period of time in a harvest season, all of the corn picked by the combine in that season (a mere few weeks). In contrast, the shelling equipment at the central shelling station need only be large enough to shell the same quantity of corn over a year-long period. The central shelling station is, of course, scaled up to handle the quantity of corn previously shelled by a multitude of combines. However, even if one assumes conservatively that the shelling equipment in the combines will be operated for a period of two months, the shelling equipment at a central shelling station operated all year long need only have one-sixth the cumulative shelling capacity of the multitude of combines replaced by the central shelling station. Moreover, as previously noted, the central shelling station conserves the petroleum-based fuel consumed by the combines to move the weight of the shelling equipment thereon up and down rows in the cornfields. Conservation of fuel in this manner can be quite substantial because the weight of the shelling equipment moved up and down corn rows by the combines has six times the shelling capacity of the stationary shelling equipment at the central shelling station.

Of course, all of the above-noted reductions in the consumption of petroleum-based fuel also reduce costs. Moreover, as previously noted, the central shelling station will most likely be powered by electricity. This presents an opportunity for reducing operating expenses by maximizing the operation of the shelling equipment during late night and early morning hours when electricity rates are lower.

Factors which offset some of the cost savings and fuel conservation described above are the cost of transporting to the central shelling station that part of the ear corn attributable to the weight and/or volume of the corn cobs, and the fuel consumed in doing so. These are incremental items of transportation cost and fuel consumption. The cost of transporting that part of the ear corn attributable to the corn kernels, and the fuel consumed in doing so, were already part of the transportation cost and fuel consumption when shelled corn from combines was transported to the ethanol manufacturing facility.

Another factor partially offsetting the cost savings described above arises when a farmer raises both corn and soy beans and needs a combine to harvest the soy beans. A farmer who has replaced the combine with an ear corn harvester would need to contract out the combining of soy beans.

Tabulated below is a summary of the effect of the present invention on costs and on the consumption of natural gas or petroleum-based fuel.

| Feature of the Present Invention | Effect on Consumption of natural gas or petroleum-based fuel | Effect on Costs |
|---|---|---|
| Use of corn cobs as fuel in the ethanol manufacturing process | Decreased | Decreased |
| Shelling at a central shelling station instead of shelling with a multitude of combines | Decreased | Decreased |
| Picking corn with an ear corn harvester instead of with a combine | Decreased | Decreased |
| Transporting ear corn to the central shelling station | Increased | Increased |

Because of the efficiencies of scale and other factors discussed above, the cost of shelling ear corn at a central shelling station should be substantially less than the cost of employing a multitude of combines to perform the shelling at each of a multitude of corn fields. The savings obtained by eliminating the cost of shelling with a combine at the corn field goes initially to the farmer. The lesser cost of shelling at the central shelling station is borne by the ethanol processor, at least initially. However, the cost of shelling at a central station can be distributed proportionally among the farmers, when computing the price to be paid to the farmers for ear corn, and because the cost of shelling at the central shelling station is less than the cumulative cost of shelling at a multitude of farm fields, the farmers would still come out ahead.

In preferred embodiments of the present invention, the central shelling station is located either at the site of the ethanol manufacturing facility or adjacent thereto. In each such instance, the central shelling station is deemed to be physically associated with the ethanol manufacturing facility. The central shelling station (CSS) can be physically removed from the ethanol manufacturing facility (EMF)

whereby shelled corn and corn cobs have to be transported by truck or rail from the CSS to the EMF, but the two locations can be otherwise associated in accordance with a broader sense of the present invention, so long as a transportation expense criterion described below is met.

There are two stages of transportation when the central shelling station is not physically associated with the ethanol manufacturing facility: (1) transportation of ear corn to the central shelling station; and (2) transportation of shelled corn and corn cobs from the central shelling station to the ethanol manufacturing facility. Part of the cost of the first transportation stage is attributable to the cost of transporting the unseparated corn cobs in the ear corn, and part of the cost of the second transportation stage is attributable to the cost of transporting the corn cobs from which the shelled corn has been separated. When (a) the combined costs from transportation stages (1) and (2), attributable to transporting the corn cobs, is less than (b) the cost savings obtained by replacing natural gas with corn cobs as the fuel for producing process heat at the ethanol manufacturing facility, the central shelling station is deemed to be associated with the ethanol manufacturing facility in accordance with the broader sense of the present invention.

Further with respect to a physically associated central shelling station, in many instances an ethanol manufacturing facility is located in a rural area where it is surrounded by farms (a) that can supply a physically associated central shelling station with ear corn and (b) that are sufficiently close so that the expense of transporting ear corn to the physically associated central shelling station becomes an insignificant factor.

Preferably, the central shelling station is operated to provide shelled corn to the ethanol manufacturing facility on a just-in-time basis in accordance with the requirements of that facility. This minimizes the need for shelled corn storage space which is typically in the form of reinforced concrete silos, or the like. It also minimizes the need for corn cob storage space, the character of which need be only rudimentary, e.g., three sides of containment walls with one open side for access by material handling equipment, such as a front end loader, and an overhanging roof to protect the cobs from rain or snow.

To the extent that storage space is required, it will be for ear corn, and the storage requirements for ear corn are not as elaborate (or expensive) as the storage requirements for shelled corn. On the other hand, the footprint and volume of the storage space for a given quantity of ear corn is substantially greater than the foot print and volume of the storage requirements for the shelled corn derived from that quantity of ear corn. However, one does not need a large inventory of ear corn to operate the central shelling station on a just-in-time basis. One need only have (1) a sufficient supply of ear corn in storage to allow operation of the central shelling station at a rate dictated by the demands of the ethanol manufacturing facility together with (2) regular, periodic deliveries of ear corn to replenish the inventory of ear corn depleted by the operation of the central shelling station.

Ideally, ear corn is delivered to the central shelling station on a just-in-time basis; this would minimize the need for ear corn storage space there. In such a situation, the bulk of the ear corn required by the central shelling station over a year's time would be stored at farms or at an intermediate storage location which performs a function for ear corn akin to that performed by a grain elevator for shelled corn.

There are benefits to storing corn as ear corn rather than as shelled corn. As noted above, the storage facility for ear corn is less elaborate than the storage facility for shelled corn which must be fully enclosed and protected from the elements. In contrast, ear corn stored on the farm (or at an intermediate storage facility) is stored in a corn crib (or equivalent storage facility) having a floor, a roof and side walls with openings to allow ambient air to circulate through the stored ear corn. Ear corn dries naturally when stored in a corn crib or the like. Depending upon the initial moisture content, drying can be substantial during the first 30 to 60 days of storage in a corn crib or the like. In contrast, shelled corn does not sufficiently dry naturally in its storage facility; instead, shelled corn must be artificially dried with a dryer that burns fuel to provide the drying heat.

More particularly, with respect to shelled corn and ear corn each harvested from a corn field at the same moisture content, and each stored in its respective storage facility for the same period of time, the ear corn will dry naturally while stored in a corn crib or the like; but shelled corn must be artificially dried to attain the same reduced moisture content as that attained by the ear corn during storage (e.g., 18% moisture or less).

Shelled corn is dried by a dryer that typically burns natural gas so that the drying process consumes an energy source that is expensive and non-renewable. If ear corn were to be shelled at the central shelling station after being dried artificially at a dryer that burns corn cobs from the sheller (as is done with seed corn in Stansfield U.S. Pat. No. 4,139,952, discussed above in the "Background" section), such a procedure would deprive the ethanol manufacturing process of an inexpensive, renewable fuel, and the corn cobs would have to be replaced there with natural gas. Thus, storing ear corn in a corn crib or the like to reduce the moisture content of the ear corn, before shelling at a central shelling station, conserves energy and reduces expense. As used herein, the term "corn crib or the like" refers to a storage facility for ear corn that allows air to circulate through the ear corn to dry the ear corn naturally. At one time, there was a rat problem associated with the storage of ear corn, but contemporary expedients for dealing with that problem have it under control.

As noted above, ideally, ear corn is delivered to the central shelling station on a just-in-time basis. In a less-preferred embodiment, a year's supply of ear corn is delivered to the central shelling station over a relatively short period of time, substantially less than a year. If the central shelling station is sized to shell ear corn over a twelve month period, then there must be sufficient storage space to accommodate the ear corn surplus until it can be shelled.

An alternative solution to the aforementioned scenario would be to increase the size of the central shelling station so that it could shell a year's supply of ear corn in substantially less than a year. This would reduce the storage space requirements for ear corn, but it would increase the storage space requirements for shelled corn and corn cobs. This alternative would also increase the capital expense for the shelling equipment at the central shelling station; but it would not eliminate all of the savings in operating expenses or all of the reduction in energy consumption obtained by employing the combination of ear corn harvesters and central shelling station, all of which is discussed in detail above. For example the stationary central shelling station still conserves the fuel consumed by combines moving the weight of their shelling equipment up and down corn rows, no matter what the size of the central shelling station.

The foregoing detailed description is a projection. It has been given for clearness of understanding only, and no unnecessary limitations should be understood therefrom, as modifications will be obvious to those skilled in the art.

The invention claimed is:

1. A method for producing ethanol and that employs corn plant material comprising cobs characterized by having previously been subjected to upstream processing that has been performed upstream of an ethanol manufacturing facility and that has comprised the steps of:

employing harvesting equipment to pick, from a plurality of farm fields, corn plant material including ear corn comprising corn and cobs as components, and to return a corn plant ingredient other than corn to the farm fields;

employing the harvesting equipment, that has picked said ear corn, to accumulate, at said farm fields, corn plant material comprising cobs;

said picking and accumulating steps being performed in a single pass of said harvesting equipment;

and delivering corn plant material comprising cobs, from a plurality of farm fields, to a downstream location that is (a) downstream of said farm fields, (b) remote from the farms where the cobs are harvested and (c) physically associated with an ethanol manufacturing facility that receives corn as a feed material;

the corn plant material delivered to said downstream location comprising a plurality of corn plant ingredients delivered together to said downstream location;

the proportion of cobs in the corn plant material delivered to said downstream location being greater than the proportion of any other stover ingredient in that material;

and wherein said method comprises the steps of:

providing an ethanol manufacturing facility with which said downstream location is physically associated and that is remote from the farms that supply said ethanol manufacturing facility with feed material;

receiving, at said downstream location, from a plurality of farm fields, corn plant material comprising cobs characterized by having undergone said upstream processing;

subjecting the material that has undergone said upstream processing to further processing at said downstream location; and employing the material that has undergone said upstream processing as a source of fuel for processing a corn plant ingredient into ethanol at an ethanol manufacturing facility with which said downstream location is physically associated;

there being no consumption, of a corn plant ingredient that has undergone said upstream processing, to dry corn at said downstream location.

2. A method for producing ethanol from corn in a process that uses heat for which there has been employed, as a source of fuel, corn plant material comprising cobs characterized by having previously been subjected to upstream processing that has been performed upstream of an ethanol manufacturing facility, wherein said upstream processing has comprised the steps of:

employing harvesting equipment to pick, from a plurality of farm fields, corn plant material including ear corn comprising corn and cobs as components, and to return a corn plant ingredient other than corn to the farm fields;

employing the harvesting equipment, that has picked said ear corn, to accumulate, at said farm fields, corn plant material comprising cobs;

said picking and accumulating steps being performed in a single pass of said harvesting equipment;

and delivering corn plant material comprising cobs, from a plurality of farm fields, to a downstream location that is (a) downstream of said farm fields, (b) remote from the farms where the cobs are harvested and (c) physically associated with an ethanol manufacturing facility that receives corn as a feed material;

the corn plant material delivered to said downstream location comprising a plurality of corn plant ingredients delivered together to said downstream location;

the proportion of cobs in the corn plant material delivered to said downstream location being greater than the proportion of any other stover ingredient in that material;

and wherein said method comprises the steps of:

providing an ethanol manufacturing facility with which said downstream location is physically associated and that is remote from the farms that supply said ethanol manufacturing facility with feed material;

receiving corn, from a plurality of farm fields, as feed material at said ethanol manufacturing facility;

processing corn into ethanol at said ethanol manufacturing facility; and using, in said processing, heat for which there has been employed, as a source of fuel, corn plant material comprising cobs characterized by having been subjected to said upstream processing;

there being no consumption, of a corn plant ingredient that has been subjected to said upstream processing, to dry, at said downstream location, concurrently with cobs, corn that is processed into ethanol produced by said method;

the ethanol produced by said method being processed from corn undried, concurrently with cobs, by consumption, at said downstream location, of said corn plant ingredient that has been subjected to said upstream processing.

3. A method as recited in claim 1 or claim 2 wherein:

the corn plant material delivered to said downstream location comprises cobs as a minor portion.

4. A method as recited in claim 3 wherein:

the further processing performed at the downstream location comprises the shelling of ear corn.

5. A method as recited in claim 1 or claim 2 wherein said upstream processing has comprised:

providing a storage site downstream of the farm fields that supply the ethanol manufacturing facility with feed material;

receiving corn plant material comprising cobs at said storage site;

and storing said corn plant material comprising cobs at said storage site before said material is employed as a source of fuel at an ethanol manufacturing facility;

the proportion of cobs in said corn plant material received at the storage site being greater than the proportion of any other stover ingredient in that material.

6. A method for producing ethanol and that employs corn plant material comprising cobs characterized by having previously been subjected to upstream processing that has been performed upstream of an ethanol manufacturing facility and that has comprised the steps of:

employing harvesting equipment to pick, from a plurality of farm fields, corn plant material including ear corn comprising corn and cobs as components, and to return a corn plant ingredient other than corn to the farm fields;

and delivering corn plant material comprising cobs, from a plurality of farm fields, to a downstream location that is (a) downstream of said farm fields, (b) remote from the farms where the cobs are harvested and (c) physically associated with an ethanol manufacturing facility that receives corn as a feed material;

the corn plant material delivered to said downstream location comprising a plurality of corn plant ingredients delivered together to said downstream location;

and wherein said method comprises the steps of:

providing an ethanol manufacturing facility with which said downstream location is physically associated and that is remote from the farms that supply said ethanol manufacturing facility with feed material;

receiving, at said downstream location, from a plurality of farm fields, corn plant material comprising cobs characterized by having undergone said upstream processing;

subjecting the material that has undergone said upstream processing to further processing at said downstream location;

the corn plant material comprising cobs that is subjected to said further processing at the downstream location comprising a plurality of corn plant ingredients of which cobs are a minor portion; and employing the material that has undergone said upstream processing as a source of fuel for processing a corn plant ingredient into ethanol at an ethanol manufacturing facility with which said downstream location is physically associated;

there being no consumption, of a corn plant ingredient that has undergone said upstream processing, to dry corn at said downstream location.

7. A method as recited in claim 6 wherein:
the proportion of cobs in the corn plant material delivered to said downstream location is greater than the proportion of any other stover ingredient in that material.

8. A method as recited in claim 6 wherein:
the step of subjecting said corn plant material to further processing at the downstream location produces fuel for process heat;
and process heat obtained from said fuel is employed at a facility (i) which processes a corn plant ingredient and (ii) with which said downstream location is physically associated.

9. A method as recited in claim 8 and comprising:
directing said fuel for use in the processing of corn into ethanol at an ethanol manufacturing facility with which said downstream location is physically associated and that receives corn as a feed material.

10. A method as recited in claim 8 or claim 9 and comprising:
directing said fuel to a combustion location, in physical association with said downstream location, for combusting said fuel to provide said process heat.

11. A method as recited in claim 6 wherein:
the step of subjecting said corn plant material to further processing at the downstream location produces fuel for providing thermal energy;
and thermal energy obtained from said fuel is employed at said facility (i) that processes a corn plant ingredient into ethanol and (ii) with which said downstream location is physically associated.

12. A method as recited in claim 6 wherein said upstream processing has comprised:
removing, from a farm field in said plurality of farm fields, corn plant material comprising cobs that has undergone said upstream processing, for delivery of that material to said downstream location and for employment of that material as said source of fuel;
the proportion of cobs, in the corn plant material removed from said farm field, being greater than the proportion of any other stover ingredient in that material;
and retaining stover in said farm field.

13. A method as recited in any of claims 1, 2 and 6 wherein:
the proportion of cobs, in said corn plant material employed as said source of fuel, is greater than the proportion of any other stover ingredient in that material.

14. A method as recited in any of claim 1, 2 or 6 wherein:
said harvesting equipment is an ear corn harvester;
ear corn from said harvesting equipment has been allowed to dry naturally, in a storage facility for ear corn, before delivery to said downstream location;
and said downstream location comprises a central shelling station where ear corn from a plurality of farm fields is separated into its components.

15. A method as recited in any of claims 1, 2 and 6 wherein:
the corn plant material employed as said source of fuel comprises a plurality of corn plant ingredients of which cobs are a minor portion, and the proportion of cobs in that material is greater than the proportion of any other stover ingredient in that material.

16. A method as recited in any of claims 1, 2 and 6 wherein:
the corn plant material subjected to said further processing comprises a plurality of corn plant ingredients of which cobs are a minor portion, and the proportion of cobs in that material is greater than the proportion of any other stover ingredient in that material.

17. A method as recited in claim 1 or claim 6 wherein:
the proportion of cobs to other stover ingredients, in the material subjected to said further processing, is greater than the proportion of cobs to other stover ingredients in the stover of the corn plant.

18. A method for producing ethanol and that employs corn plant material comprising cobs characterized by having previously been subjected to upstream processing that has been performed upstream of an ethanol manufacturing facility and that has comprised the steps of:

employing harvesting equipment to pick, from a plurality of farm fields, corn plant material including ear corn comprising corn and cobs as components, and to return a corn plant ingredient other than corn to the farm fields;

and delivering corn plant material comprising cobs, from a plurality of farm fields, to a downstream location that is (a) downstream of said farm fields, (b) remote from the farms where the cobs are harvested and (c) physically associated with an ethanol manufacturing facility that receives corn as a feed material;

the corn plant material delivered to said downstream location comprising a plurality of corn plant ingredients delivered together to said downstream location;

and wherein said method comprises the steps of:

receiving, at said downstream location, from a plurality of farm fields, corn plant material comprising cobs characterized by having undergone said upstream processing;

subjecting the material that has undergone said upstream processing to further processing at said downstream location to produce a fuel for providing thermal energy;

the corn plant material comprising cobs that is subjected to said further processing at the downstream location comprising a plurality of corn plant ingredients of which cobs are a minor portion; and directing fuel produced by said further processing for use at an ethanol manufacturing facility with which said downstream location is physically associated and that receives corn as a feed material;

there being no consumption of a corn plant ingredient that has undergone said upstream processing to dry corn at said downstream location.

19. A method as recited in claim 18 wherein:

the fuel produced by said further processing step is a solid fuel;

and there is no consumption of said fuel upstream of said ethanol manufacturing facility that receives corn as a feed material.

20. A method as recited in claim 18 and comprising:

producing a residual material from feed material received at an ethanol manufacturing facility with which said downstream location is physically associated;

there being no consumption of said residual material as fuel at the ethanol manufacturing facility that receives said feed material.

21. A method as recited in claim 18 wherein:

in the manufacture of ethanol produced by said method, there is no consumption of cobs, at said downstream location, to dry, concurrently with corn, the cobs in the corn plant material subjected to said further processing;

the ethanol produced by said method employing, as the material subjected to further processing, corn plant material comprising cobs undried, concurrently with corn, by the consumption of cobs at said downstream location.

22. A method for producing ethanol from corn and that employs fuel produced, from corn plant material comprising cobs, in upstream processing that has been performed upstream of an ethanol manufacturing facility that receives corn as a feed material, wherein said upstream processing has comprised the steps of:

employing harvesting equipment to pick, from a plurality of farm fields, corn plant material including ear corn comprising corn and cobs as components, and to return a corn plant ingredient other than corn to the farm fields;

delivering corn plant material comprising cobs, from a plurality of farm fields, to a downstream location that is (a) downstream of said farm fields, (b) remote from the farms where the cobs are harvested and (c) physically associated with an ethanol manufacturing facility that receives corn as a feed material;

the corn plant material delivered to said downstream location comprising a plurality of corn plant ingredients delivered together to said downstream location;

subjecting said corn plant material comprising cobs, that has been delivered to said downstream location, to further processing at the downstream location to produce a fuel for providing thermal energy;

the corn plant material comprising cobs that is subjected to said further processing at the downstream location comprising a plurality of corn plant ingredients of which cobs are a minor portion;

and directing fuel produced by said further processing to an ethanol manufacturing facility that receives corn as a feed material;

and wherein said method comprises the steps of:

providing an ethanol manufacturing facility with which said downstream location is physically associated and that is remote from the farms that supply said ethanol manufacturing facility with feed material;

receiving the fuel, produced at said downstream location, for delivery to a combustion location where the fuel is to be combusted for thermal energy;

receiving, at said ethanol manufacturing facility, corn from a plurality of farm fields;

and processing said corn into ethanol at said ethanol manufacturing facility;

there being no consumption of a corn plant ingredient, in the corn plant material comprising cobs that has been delivered to said downstream location, to dry, at the downstream location, corn that is processed into ethanol produced by said method.

23. A method as recited in claim 22 and comprising:

providing a combustion location, physically associated with said ethanol manufacturing facility, for combusting said fuel to provide thermal energy for processing said corn into ethanol.

24. A method as recited in claim 22 wherein:

the fuel, received for delivery to said combustion location, is a solid fuel;

there is no consumption of said fuel upstream of said ethanol manufacturing facility;

and said method comprises using, in the processing of corn into ethanol, heat derived from said fuel.

25. A method as recited in claim 22 wherein:

the fuel, received for delivery to said combustion location, is a solid fuel;

there is no consumption of said fuel other than at a location that is physically associated with said ethanol manufacturing facility;

and said method comprises using, in the processing of corn into ethanol, heat derived from said fuel.

26. A method as recited in claim 22 wherein:

the ethanol produced by said method is processed from corn undried by consumption, at said downstream location, of a corn plant ingredient in the corn plant material comprising cobs that has been delivered to said downstream location.

27. A method as recited in claim 18 or claim 22 wherein:

the proportion of cobs, in the corn plant material delivered to said downstream location, is greater than the proportion of any other stover ingredient in that material;

and the proportion of cobs, in the corn plant material subjected to further processing to produce said fuel, is greater than the proportion of any other stover ingredient in that material.

28. A method as recited in claim 18 or claim 22 wherein said upstream processing has comprised:

removing said corn plant material comprising cobs from said farm fields;

there being no physical processing of cobs at a farm at which cobs are harvested following the removal of cobs from the farm field of that farm.

29. A method for producing ethanol and that employs corn plant material comprising cobs harvested from farm fields, said method comprising the steps of:

receiving said corn plant material comprising cobs at a downstream location that is (a) downstream of a plurality of farm fields that supply said location with said corn plant material comprising cobs, (b) remote from the farms at which said cobs were harvested and (c)

physically associated with an ethanol manufacturing facility that receives corn as a feed material;

subjecting the corn plant material comprising cobs that is received at said location to processing at that location;

the corn plant material comprising cobs that is subjected to said processing comprising a plurality of corn plant ingredients received together at said location and having cobs as a minor portion;

the proportion of cobs in the corn plant material subjected to said processing being greater than the proportion of any other stover ingredient in that material;

and employing the corn plant material comprising cobs that is received at said location as a source of fuel for processing a corn plant ingredient into ethanol at an ethanol manufacturing facility with which said location is physically associated;

there being no consumption of a corn plant ingredient, in the corn plant material comprising cobs received at said location, to dry corn at that location.

30. A method as recited in claim 29 wherein:

the step of subjecting said corn plant material comprising cobs to said processing produces a fuel for providing thermal energy;

and said method comprises directing fuel produced by said processing for use at an ethanol manufacturing facility with which said location is physically associated and that receives corn as a feed material.

31. A method as recited in claim 29 wherein:

the step of subjecting said corn plant material to said processing produces fuel for process heat;

and said method comprises directing to a combustion location, in physical association with said downstream location, for combusting said fuel to provide said process heat.

32. A method for producing ethanol from corn in a process that uses heat for which there has been employed fuel produced, in upstream processing, from corn plant material comprising cobs harvested from farm fields, wherein said upstream processing has been performed upstream of an ethanol manufacturing facility that receives corn as feed material, and wherein said upstream processing has comprised the steps of:

receiving said corn plant material comprising cobs at a location that is (a) downstream of a plurality of farm fields that supply said location with said corn plan material comprising cobs, (b) remote from the farms at which said cobs were harvested and (c) physically associated with an ethanol manufacturing facility that receives corn as a feed material;

and subjecting the corn plant material comprising cobs that is received at said location to processing at that location, to produce a fuel for providing thermal energy;

the corn plant material comprising cobs that is subjected to said processing comprising a plurality of corn plant ingredients received together at said location and having cobs as a minor portion;

the proportion of cobs in the corn plant material subjected to said processing being greater than the proportion of any other stover ingredient in that material;

and wherein said method comprises the steps of:

providing an ethanol manufacturing facility with which said location is physically associated and that is remote from the farms that supply said ethanol manufacturing facility with feed material;

receiving corn, from a plurality of farm fields, as feed material at said ethanol manufacturing facility;

processing corn into ethanol at said ethanol manufacturing facility; and using, in the processing of said corn into ethanol, heat for which the fuel produced in said upstream processing has been employed as fuel for said heat;

there being no consumption of a corn plant ingredient, in the corn plant material comprising cobs that has been received at said location, to dry, at that location, corn that is processed into ethanol produced by said method.

33. A method as recited in claim 32 wherein:

the ethanol produced by said method is processed from corn undried by consumption, at said location, of a corn plant ingredient in the corn plant material comprising cobs that has been received at said location.

34. A method as recited in any of claims 1, 6, 8 and 29 wherein:

in the manufacture of ethanol produced by said method, there is no consumption of cobs, at said downstream location, to dry, concurrently with corn, the cobs in the corn plant material employed as said source of fuel;

the ethanol produced by said method employing, as said source of fuel, corn plant material comprising cobs undried, concurrently with corn, by the consumption of cobs at said downstream location.

35. A method for producing ethanol and that employs corn plant material comprising cobs harvested from farm fields, said method comprising the steps of:

receiving said corn plant material comprising cobs at a downstream location that is (a) downstream of a plurality of farm fields that supply said location with said corn plant material comprising cobs, (b) remote from the farms at which said cobs were harvested and (c) physically associated with an ethanol manufacturing facility that receives corn as a feed material;

subjecting the corn plant material comprising cobs that is received at said location to processing at that location to produce fuel for process heat;

the corn plant material comprising cobs that is subjected to said processing comprising a plurality of corn plant ingredients received together at said location and having cobs as a minor portion;

and directing said fuel for use in processing corn into ethanol at an ethanol manufacturing facility with which said location is physically associated and that receives corn as a feed material;

there being no consumption of a corn plant ingredient, in the corn plant material comprising cobs received at said location, to dry corn at that location;

the processing to which said corn plant material is subjected at the downstream location producing a solid fuel; and there being no consumption of said fuel upstream of said ethanol manufacturing facility that receives corn as a feed material.

36. A method for producing ethanol and that employs corn plant material comprising cobs harvested from farm fields, said method comprising the steps of:

receiving said corn plant material comprising cobs at a downstream location that is (a) downstream of a plurality of farm fields that supply said location with said corn plant material comprising cobs, (b) remote from the farms at which said cobs were harvested and (c) physically associated with an ethanol manufacturing facility that receives corn as a feed material;

subjecting the corn plant material comprising cobs that is received at said location to processing at that location to produce a fuel for process heat;

the corn plant material comprising cobs that is subjected to said processing comprising a plurality of corn plant ingredients received together at said location and having cobs as a minor portion;

and directing said fuel for use in processing corn into ethanol at an ethanol manufacturing facility with which said location is physically associated and that receives corn as a feed material;

producing a residual material from feed material received at an ethanol manufacturing facility with which said downstream location is physically associated;

there being no consumption of said residual material as fuel at the ethanol manufacturing facility that receives said feed material;

there being no consumption of a corn plant ingredient, in the corn plant material comprising cobs received at said downstream location, to dry corn at that location.

37. A method for employing, in the production of ethanol from corn, corn plant material comprising cobs harvested from farm fields that grow corn, said method comprising the steps of:

providing an ethanol manufacturing facility that receives corn as a feed material;

said ethanol manufacturing facility being remote from the farms that supply said ethanol manufacturing facility with feed material;

said ethanol manufacturing facility being physically associated with a location (a) that is downstream of a plurality of farm fields that grow corn, (b) that receives corn plant material comprising cobs from said farm fields and (c) that is remote from the farms where the cobs are harvested;

receiving, at said ethanol manufacturing facility, corn from a plurality of farm fields;

processing said corn into ethanol at said ethanol manufacturing facility;

using, in said processing, heat obtained from fuel for which there has been employed, as a source, corn plant material comprising cobs received at said location;

the corn plant material employed as said source of fuel comprising a plurality of corn plant ingredients received together at said location and having cobs as a minor portion;

the proportion of cobs in the corn plant material employed as said source of fuel being greater than the proportion of any other stover ingredient in that material;

there being no consumption of a corn plant ingredient, in the corn plant material comprising cobs employed as said source of fuel, to dry, at said location, corn that is processed into ethanol produced by said method;

the ethanol produced by said method being processed from corn undried, by consumption at said location, of a corn plant ingredient in the corn plant material comprising cobs that has been employed as said source of fuel.

38. A method as recited in claim 37 wherein:

in the manufacture of ethanol produced by said method, there is no consumption of cobs, at said location, to dry, concurrently with corn, the cobs in the corn plant material employed as said source of fuel;

the ethanol produced by said method employing, as said source of fuel, corn plant material comprising cobs undried, concurrently with corn, by the consumption of cobs at said location.

39. A method for employing, in the production of ethanol, corn plant material comprising cobs harvested from farm fields, said method comprising the steps of:

providing a location that is (a) downstream of a plurality of farm fields that supply said location with corn plant material comprising cobs, (b) remote from the farms at which the cobs were harvested and (c) physically associated with an ethanol manufacturing facility that receives corn as a feed material;

receiving, at said location, from said plurality of farm fields, corn plant material comprising cobs;

the corn plant material comprising cobs received at said location comprising a plurality of corn plant ingredients received together at said location;

the proportion of cobs in said corn plant material received at said location being greater than the proportion of any other stover ingredient in that material;

subjecting the corn plant material comprising cobs received at said location to processing at said location to produce fuel for process heat;

processing a corn plant ingredient into ethanol at an ethanol manufacturing facility with which said location is physically associated;

using, in said processing, heat obtained from fuel produced by the processing of said corn plant material comprising cobs at said location;

there being no consumption, at said location, of a corn plant ingredient in the corn plant material comprising cobs received at said location, to dry corn there.

40. A method as recited in claim 39 and comprising:

directing said fuel for use in the processing of corn into ethanol at an ethanol manufacturing facility that receives corn as a feed material and that is physically associated with said location.

41. A method as recited in claim 39 wherein:

the proportion of cobs to other stover ingredients, in the corn plant material comprising cobs subjected to said processing at said location, is greater than the proportion of cobs to other stover ingredients in the stover of the corn plant.

42. A method for employing, in the production of ethanol from corn, corn plant material comprising cobs harvested from farm fields, said method comprising the steps of:

providing an ethanol manufacturing facility that is physically associated with a location (a) that receives corn plant material comprising cobs from a plurality of corn fields that are upstream of said location, (b) that is remote from the farms at which the cobs were harvested and (c) at which said corn plant material comprising cobs is processed to produce fuel for process heat;

said ethanol manufacturing facility being remote from the farms that provide said facility with feed material;

receiving corn, from a plurality of farm fields, as feed material at said ethanol manufacturing facility;

processing corn into ethanol at said ethanol manufacturing facility;

using, in said processing, heat obtained from fuel produced by the processing of said corn plant material comprising cobs at said location;

the corn plant material processed to produce said fuel comprising a plurality of corn plant ingredients received together at said location;

the proportion of cobs in that corn plant material being greater than the proportion of any other stover ingredient in that material;

there being no consumption of a corn plant ingredient, in said corn plant material comprising cobs, to dry, at said location, concurrently with cobs, corn that is to be processed into ethanol by said method;

the ethanol produced by said method being processed from corn undried, concurrently with cobs, by the consumption, at said location, of a corn plant ingredient in said corn plant material comprising cobs.

43. A method as recited in claim 39 or claim 42 wherein: the plurality of corn plant ingredients received together at said location comprises cobs as a minor portion.

44. A method for employing, in the production of ethanol, corn plant material comprising cobs harvested from farm fields, said method comprising the steps of:
   providing a location that is (a) downstream of a plurality of farm fields that supply said location with corn plant material comprising cobs, (b) remote from the farms where the cobs are harvested and (c) physically associated with an ethanol manufacturing facility that receives corn as a feed material;
   receiving, at said location, from said plurality of farm fields, corn plant material comprising cobs;
   the corn plant material comprising cobs received at said location comprising a plurality of corn plant ingredients received together at said location and having cobs as a minor portion;
   subjecting the corn plant material comprising cobs received at said location to processing at said location to produce fuel for process heat;
   and directing said fuel for use in the processing of corn into ethanol at an ethanol manufacturing facility that is physically associated with said location and that receives corn as a feed material;
   there being no consumption, at said location, of a corn plant ingredient, in the corn plant material comprising cobs received at said location, to dry corn there.

45. A method for employing, in the production of ethanol from corn, corn plant material comprising cobs harvested from farm fields that grow corn, said method comprising the steps of:
   providing an ethanol manufacturing facility that receives corn as a feed material;
   said ethanol manufacturing facility being remote from the farms that supply said ethanol manufacturing facility with feed material;
   said ethanol manufacturing facility being physically associated with a location (a) that is downstream of a plurality of farm fields that grow corn, (b) that receives corn plant material comprising cobs from said farm fields and (c) that is remote from the farms where the cobs are harvested;
   receiving, at said ethanol manufacturing facility, corn from a plurality of farm fields;
   processing said corn into ethanol at said ethanol manufacturing facility;
   using, in said processing, heat obtained from fuel for which there has been employed, as a source, corn plant material comprising cobs received at said location;
   the corn plant material employed as said source of fuel comprising a plurality of corn plant ingredients received together at said location and having cobs as a minor portion;
   there being no consumption of a corn plant ingredient, in the corn plant material comprising cobs employed as said source of fuel, to dry, at said location, corn that is processed into ethanol produced by said method;
   the ethanol produced by said method being processed from corn undried, by consumption at said location, of a corn plant ingredient in the corn plant material comprising cobs that has been employed as said source of fuel.

* * * * *

UNITED STATES PATENT AND TRADEMARK OFFICE
CERTIFICATE OF CORRECTION

PATENT NO. : 10,000,777 B2
APPLICATION NO. : 14/710293
DATED : June 19, 2018
INVENTOR(S) : Alvin D. Shulman Page 1 of 1

It is certified that error appears in the above-identified patent and that said Letters Patent is hereby corrected as shown below:

In the Claims

In Claim 31, at Column 17, Line 31, please insert -- said fuel -- after the word "directing."

Signed and Sealed this
Seventh Day of May, 2019

Andrei Iancu
*Director of the United States Patent and Trademark Office*